(12) United States Patent
Tuman, III

(10) Patent No.: US 11,152,088 B2
(45) Date of Patent: Oct. 19, 2021

(54) METHODS, SYSTEMS AND COMPUTER PROGRAM PRODUCTS FOR ELECTRONIC DATA ENTRY

(71) Applicant: John Tuman, III, Wilmington, NC (US)

(72) Inventor: John Tuman, III, Wilmington, NC (US)

(73) Assignee: Novant Health, Inc., Winston-Salem, NC (US)

( * ) Notice: Subject to any disclaimer, the term of this patent is extended or adjusted under 35 U.S.C. 154(b) by 131 days.

(21) Appl. No.: 16/246,889

(22) Filed: Jan. 14, 2019

(65) Prior Publication Data

US 2020/0227146 A1  Jul. 16, 2020

(51) Int. Cl.

| | |
|---|---|
| *G16H 10/60* | (2018.01) |
| *G10L 15/30* | (2013.01) |
| *G10L 15/18* | (2013.01) |
| *G10L 15/22* | (2006.01) |
| *G16H 15/00* | (2018.01) |
| *H04L 29/08* | (2006.01) |

(52) U.S. Cl.
CPC ......... *G16H 10/60* (2018.01); *G10L 15/1822* (2013.01); *G10L 15/22* (2013.01); *G10L 15/30* (2013.01); *G10L 2015/223* (2013.01); *H04L 67/06* (2013.01)

(58) Field of Classification Search
CPC ........ G16H 10/10; G16H 10/20; G16H 10/40; G16H 10/60; G16H 10/65; G16H 15/00; G16H 15/28; G16H 15/285; G16H 15/30; G16H 15/32; G16H 15/34; G10L 15/08; G10L 15/18; G10L 15/221; G10L 15/222; G10L 15/26; G10L 15/265; G10L 15/183; G10L 15/187; G10L 15/19; G10L 15/193; G10L 15/197; G10L 15/28; G10L 15/285; G10L 2015/223; G10L 2015/225; G10L 2015/226; G10L 2015/227; G10L 2015/228; G10L 15/30; G10L 15/1822; G10L 15/22; H04L 67/02; H04L 67/06
USPC ....... 704/201, 8, 9, 211, 231, 232, 233, 234, 704/235, 246, 251; 710/62, 72, 73, 74
See application file for complete search history.

(56) References Cited

U.S. PATENT DOCUMENTS

| | | | |
|---|---|---|---|
| 2009/0049610 A1* | 2/2009 | Heimbrock | A61G 7/015 5/600 |
| 2015/0125832 A1* | 5/2015 | Tran | G09B 19/0092 434/127 |
| 2017/0124348 A1* | 5/2017 | Pourzandi | H04L 9/008 |
| 2017/0249432 A1* | 8/2017 | Grantcharov | H04L 63/0272 |
| 2018/0330115 A1* | 11/2018 | Felton | G16H 10/60 |

* cited by examiner

*Primary Examiner* — Leshui Zhang
(74) *Attorney, Agent, or Firm* — Myers Bigel, P.A.

(57) ABSTRACT

A system is provided for recording electronic data records including an interactive audio interface configured to receive a real time voice command, parse the real time voice command for keywords and values and trigger the values to be stored; an external database configured to store the values parsed from the real time voice command and associate a time stamp with the stored values; a secure file transfer tool configured to transfer the stored values and time stamp to a secure datacenter; and an electronic records module in the secure datacenter configured to store the values in corresponding data records. Related methods and systems are also provided herein.

15 Claims, 5 Drawing Sheets

METHODS, SYSTEMS AND COMPUTER PROGRAM PRODUCTS FOR ELECTRONIC DATA ENTRY

FIELD

The inventive concept relates generally to data entry and storage and, more particularly, to methods and systems for using smart speakers to obtain and store data.

BACKGROUND

The value of data is becoming more important in today's society. Internet shopping websites collect data on customers and tailor advertising based on the collected data. Utilities collect data on customers to determine how much water, gas, electric etc. is being used. Doctors and hospitals collect data from patients related to insurance information, personal health information, family health history and the like. Some of this data, for example, the internet data, is collected without any knowledge of the customer. In other words, Internet shopping cites install "cookies" on a customer's machine and the data is collected in the background and does not require any data entry. Similarly, the utilities collect data in meters associated with the customer premises, but don't actually physically record the data. However, in patient care, much of the information is still hand entered into a machine by a doctor, nurse, patient or care taker. Manual data entry is time consuming and can result in human error when the incorrect information is written down or the wrong box is checked. Improved methods and systems for data entry, particularly in the healthcare field, are desired.

SUMMARY

Some embodiments of the inventive concept provide a system for recording electronic data records including an interactive audio interface configured to receive a real time voice command, parse the real time voice command for keywords and values and trigger the values to be stored; an external database configured to store the values parsed from the real time voice command and associate a time stamp with the stored values; a secure file transfer tool configured to transfer the stored values and time stamp to a secure datacenter; and an electronic records module in the secure datacenter configured to store the values in corresponding data records.

In further embodiments, an electronic interface may be provided in the secure datacenter that is configured to receive the transferred stored values and time stamp from the secure file transfer tool and determine a physical location associated with the stored values and the time stamp. In these embodiments, the physical location may be one of a room number, bed number and any identifier of physical location associated with the interactive audio interface and the physical location may be located by matching an identifier associated with the interactive audio interface to the physical location in a look up table.

In still further embodiments, the database may be further configured to store a physical location of the interactive audio interface associated with the stored values with the stored values and the time stamp. In these embodiments, the physical location may be one of a room number, bed number and any identifier of physical location associated with the interactive audio interface and the physical location may be located by matching an identifier associated with the interactive audio interface to the physical location in a lookup table.

In some embodiments, the stored values in the electronic records module may be verified before becoming a permanent part of the data record.

In further embodiments, the electronic records module may include an electronic medical records data module and the data records may be patient data records.

In still further embodiments, the interactive audio interface may be further configured to receive request for patient satisfaction applications and/or information and provide the requested patient satisfaction applications and/or information.

Related methods and computer program products are also provided herein.

DETAILED DESCRIPTION OF SOME EMBODIMENTS

Figure 1:
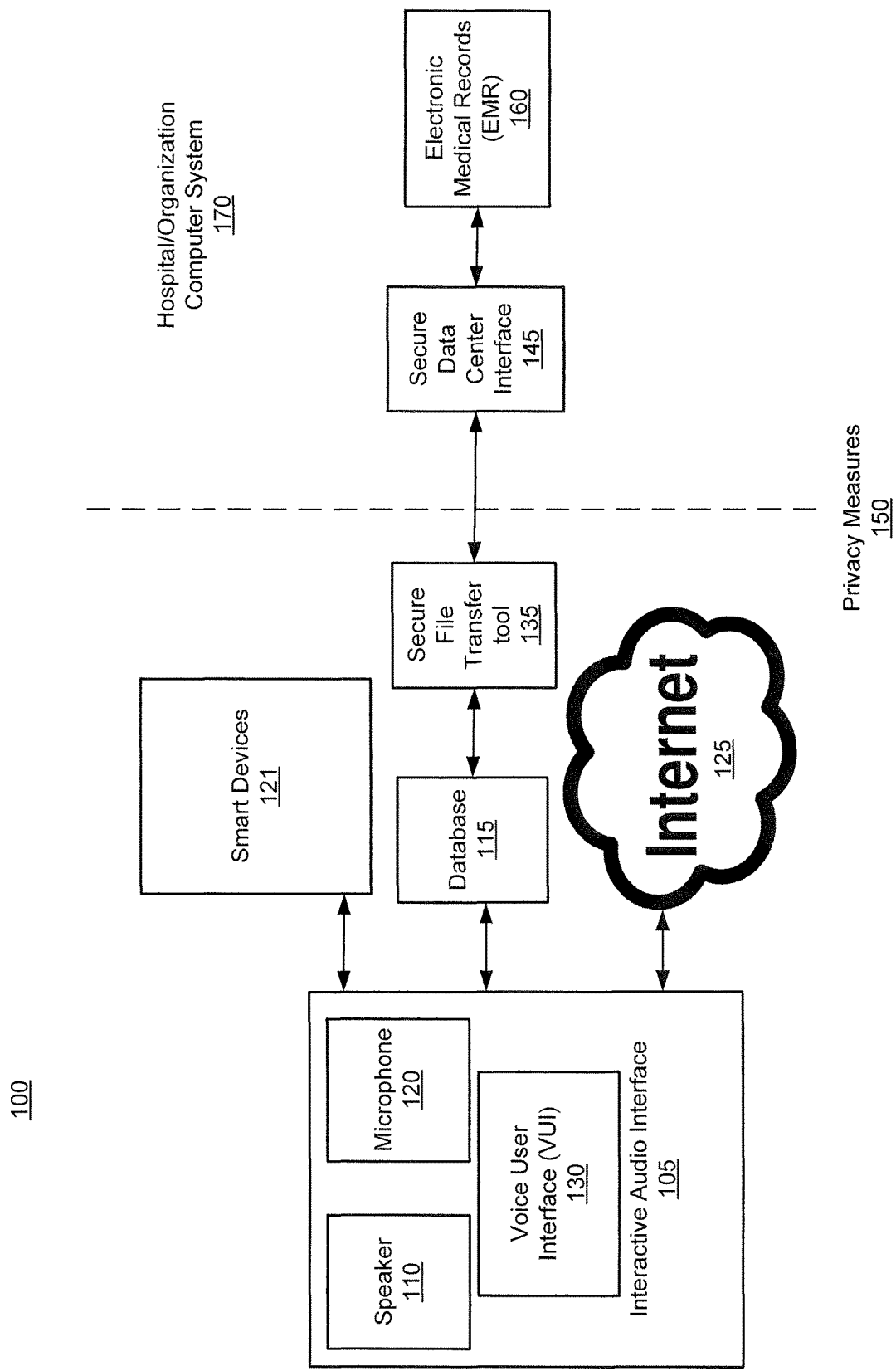
FIG. 1 is a simple block diagram of a system in accordance with some embodiments of the present inventive concept(s).

Specific example embodiments of the inventive concept now will be described with reference to the accompanying drawings. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. In the drawings, like numbers refer to like elements. It will be understood that when an element is referred to as being "connected" or "coupled" to another element, it can be directly connected or coupled to the other element or intervening elements may be present. As used herein the term "and/or" includes any and all combinations of one or more of the associated listed items.

The terminology used herein is for the purpose of describing particular embodiments only and is not intended to be limiting of the inventive concept. As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the specification and the relevant art and will not be interpreted in an idealized or overly formal sense unless expressly so defined herein.

As discussed above, as the world we live in becomes more virtual, the value of data continues to increase. Accurate entry and storage of data is becoming increasingly more important as this data is used to make decisions that can change the direction of a company, a doctor, a teacher and the like. Although embodiments of the present inventive concept are not limited to use in the healthcare field, embodiments of the present inventive concept will be discussed herein with respect to the healthcare/clinical environment. The clinical environment provides a relevant test case for all aspects of the present inventive concept as it involves entry and storage of large amounts of data that must be kept confidential due to privacy laws, such as the Health Insurance Portability and Accountability Act (HIPAA). Thus, embodiments discussed herein do not only address entry and storage issues, but privacy issues as well.

In particular, the current method of entering patient data into a database typically involves as clinician manually entering data into a user interface of a computer system. As used herein, a "clinician" refers to anyone who can enter data into a system for a patient that is associated with the hospital, for example, a clinician may be a doctor, nurse, nurse's aide, administrator and the like. It will be further understood that, in some circumstances, the patient may enter data into the system himself. Various graphical user interfaces are available that allow data to be entered more rapidly by clicking a series of buttons or checking boxes, but the data entry process is still time consuming and subject to error. Sometimes a clinician will dictate or record patient information and spend time at the end of the day "charting" that data. This can also be very time consuming and adds to the clinicians' already stressful day.

Thus, the current method of entering data generally demands too much time away from the primary responsibility of the clinician, which is to define and execute care plans and care for the patient. The current approach requires training, practice and repetition to learn how to enter data into the electronic medical record (EMR). As discussed above, programmers have been enlisted to design screen layouts to reduce the "number of clicks" required to enter and access medical information from the EMR to improve clinical efficiencies. Because the value of the data is not diminishing, but increasing, more data entry in all parts of life will likely be required. With this increase in demand, the present methods available for data entry is an obstacle for clinicians leading them to have feelings of being overwhelmed and having to compromise between proper data entry and compliance activities and direct patient care. Thus, improved methods of data entry are desired.

Accordingly, some embodiments of the present inventive concept provide methods, systems and computer program products that enable hands-free data entry into a patient record by the clinician in "real-time." As used herein "real-time" refers to processing data within milliseconds so that it is appears to happen virtually immediately. As will be discussed further herein, this data is entered and stored in full compliance with all patient privacy concerns dictated by HIPAA.

As will be discussed further below with respect to the figures, some embodiments of the present inventive concept use an interactive audio interface (or smart speaker) to enter patient related data. The interactive audio interface may be provided by, for example, an Amazon Echo or Dot, Google Home, Apple HomePod or the like without departing from the scope of the present inventive concept. In some embodiments, in addition to increasing clinical productivity, the interactive audio interface may be used to provide music, soothing sounds, audible books, games, news, sports, weather and the like to the patient to improve patient satisfaction. The interactive audio interface may also be configured to provide answers to commonly asked questions providing on-demand information and reducing interruptions for clinicians, especially the nursing staff. For example, patients and guests could ask the interactive audio interface about, "visiting hours", "dining options", "TV channel guide", medication information for commonly prescribed medications, and the like.

Referring first to FIG. 1, a simplistic diagram of a system 100 in accordance with some embodiments of the present inventive concert will be discussed. As illustrated in FIG. 1, the system 100 includes an interactive audio interface 105, smart devices 121, an internet cloud 125, a database 115, a secure file transfer tool 135, and an organization computer system 170. As illustrated, the interactive audio interface 105 may include a speaker 110, a microphone 120 and a voice user interface (VUI) 130. The interactive audio interface 105 may be provided by an Amazon Echo, Google Home, ApplePod or may be custom designed without departing from the scope of the present inventive concept. Embodiments of the present inventive concept will be discussed herein with respect to the Amazon Echo, however, embodiments of the present inventive concept are not limited thereto.

The interactive audio interface 105 can be used to control smart devices 121, such as televisions, lighting, thermostats, door locks, entertainment systems and the like. Using the interactive audio interface 105 to control the smart devices 121 may allow the patient to have increased satisfaction in the patient experience. As further illustrated in FIG. 1, the interactive audio interface 105 is coupled to the Internet 125. The interactive audio interface 105 receives voice commands from the user (patient, clinician or guest) at the speaker 110 and interprets the voice commands with the voice user interface 130. Coupling the interactive audio interface 105 to the Internet 125 allows the user full access to applications on the internet, such as music applications, weather applications, new applications, and other types of information available on the internet. The interactive audio interface 105 may provide the requested information utilizing the speaker 110. As illustrated in FIG. 1, the smart devices 121 and the Internet 125 are provided on a same side of the privacy measures 150 as the interactive audio interface 105.

The hospital's/organization's computer system 170 is provided on an opposite side of the privacy measures 150, embodiments of which will be discussed further below. As illustrated, the hospitals computer system 170 includes a secure datacenter interface 145 and an EMR 160. In accordance with some embodiments of the present inventive concept, the VUI 130 is further configured to recognize specific commands associated with electronic medical records 160 and record the data associated with each of the commands in the EMR 160 utilizing privacy measures 150 that anonymize the data, but store the data in the correct record associated with the correct patient. Once stored, the data can then be verified by a clinician before being permanently stored in the EMR. In other words, embodiments of the present inventive concept allow a clinician to verbally activate the interactive audio interface 105 using custom commands associated with patient data and store this verbally received data in the correct patient records in the EMR 160 without violated HIPAA privacy laws.

In particular, the interactive audio interface 105 may be configured to recognize a command, much like "Alexa", that will engage the data entry function. Once the interactive audio interface 105 recognizes that the information being spoken relates to patient records, the interactive audio interface 105 listens for the key words associated with specific patient data and begins a process to store the patient data in the correct patient record.

For purposes of example only, the interactive audio interface 105 will be referred to as "Margaret." It will be understood that embodiments of the present inventive concept are not limited by this example. Thus, the word "Margaret" will be spoken to the interactive audio interface 105 to indicate that the interface 105 will be asked to perform some function. Then, the word "chart" may be used to indicate that the "function" is data entry into a patient record. The following may be a typical order of information obtained by a clinician during a routine patient visit. "Margaret":

chart 3P's
chart Pain 5
chart POSS 2 (Pasero Opioid-induced sedation scale)
chart vitals blood pressure 120 over 80
chart vitals temperature 98.6
chart vitals pulse 72
chart urinary output 100 ml
chart meals breakfast 75%
chart activity . . . i.e. resting, turned, stand at bedside, stand and pivot, ambulate in hall, ambulate in hallway 15 feet.

When this information is spoken using the "Margaret chart" command, using embodiments discussed herein, the patient information spoken will be stored in the proper patient record in the EMR 160 in compliance with HIPAA.

Thus, using natural language processing technology in the form of an interactive audio interface 105 data entry for discrete data elements may be performed using oral commands. However, is some embodiments, the interactive audio interface may be configured to recognize dictation or to intelligently parse conversations to select medically relevant data elements for documentation. Accordingly, utilizing interactive audio interfaces as discussed above may provide improved clinical efficiency, patient and clinical satisfaction, reduce burn-out as well as an overall better outcome.

Figure 2:
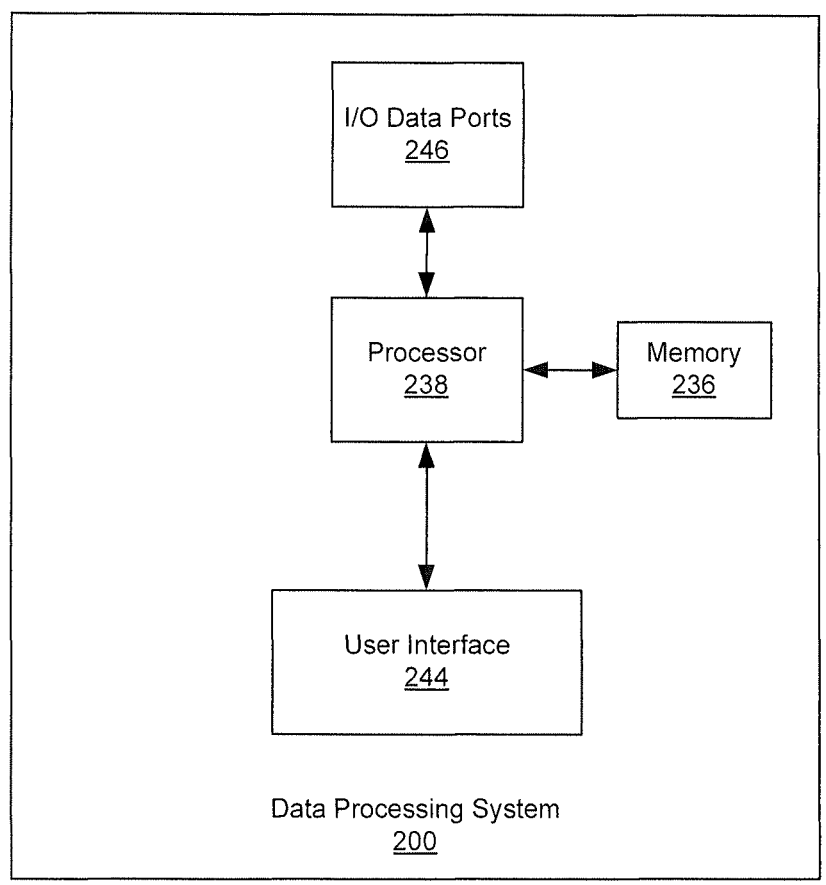
FIG. 2 is a block diagram of a data processing system according to embodiments of the present inventive concept(s).
Figure 3:
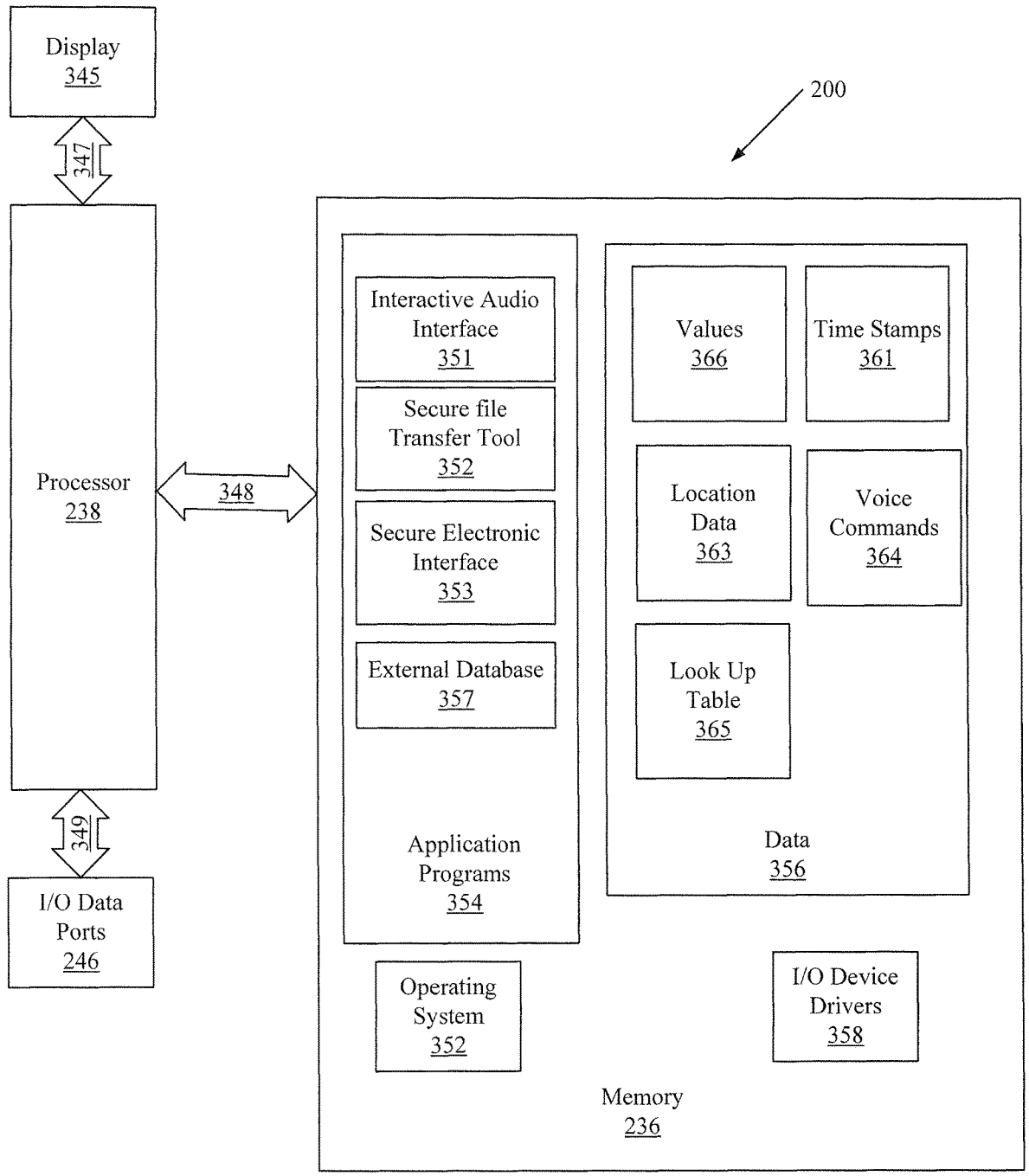
FIG. 3 is a more detailed block diagram of the data processing system illustrated in FIG. 2 in accordance with some embodiments of the present inventive concept(s).

Referring now to FIGS. 2 and 3, a data processing system 200 that may be used in the system 100 illustrated in FIG. 1 in accordance with some embodiments of the inventive concept will be discussed. The data processing system 200 may be included any element of the system 100 without departing from the scope of the present inventive concept. As illustrated in FIG. 2, an exemplary embodiment of a data processing system 200 suitable for use in the system 100 of FIG. 1 includes a user interface 244 such as a keyboard, keypad, touchpad or the like, I/O data ports 246 and a memory 236 that communicates with a processor 238. The I/O data ports 246 can be used to transfer information between the data processing system 200 and another computer system or a network. These components may be conventional components, such as those used in many conventional data processing systems, which may be configured to operate as described herein.

Referring now to FIG. 3, a more detailed block diagram of the data processing system 200 in accordance with some embodiments of the present inventive concept will be discussed. The processor 238 communicates with a display 345 via and address/data bus 347, the memory 236 via an address/data bus 348 and the I/O data ports 246 via an address/date bus 349. The processor 238 can be any commercially available or custom microprocessor or ASICs. The memory 236 is representative of the overall hierarchy of memory devices containing the software and data used to implement the functionality of the data processing system 200. The memory 236 can include, but is not limited to, the following types of devices: cache, ROM, PROM, EPROM, EEPROM, flash memory, SRAM, and DRAM.

As shown in FIG. 3, the memory 236 may include several categories of software and data used in the data processing system 200: an operating system 352; application programs 354; input/output (I/O) device drivers 358; and data 356. As will be appreciated by those of skill in the art, the operating system 352 may be any operating system suitable for use with a data processing system, such as OS/2, AIX or zOS from International Business Machines Corporation, Armonk, N.Y., Windows95, Windows98, Windows2000, WindowsXP, Vista, Windows 7, Windows 8 or Windows 10 from Microsoft Corporation, Redmond, Wash., Unix, Linux, LabView, or a real-time operating system such as QNX or VxWorks, or the like. The I/O device drivers 358 typically include software routines accessed through the operating system 352 by the application programs 354 to communicate with devices such as the I/O data port(s) 246 and certain memory 236 components. The application programs 354 are illustrative of the programs that implement the various features of the data processing system 200 included a system in accordance with some embodiments of the present inventive concept and preferably include at least one application that supports operations according to some embodiments of the present inventive concept. Finally, the data 356 represents the static and dynamic data used by the application programs 354, the operating system 352, the I/O device drivers 358, and other software programs that may reside in the memory 236.

As illustrated in FIG. 3, the data 356 according to some embodiments of the present inventive concept may include values 366, time stamps 361, location data 363, voice commands 364 and lookup tables 365. Although the data 356 illustrated in FIG. 3 includes five different files 366, 361, 363, 364 and 365 embodiments of the present inventive concept are not limited to this configuration. Two or more files may be combined to make a single file; a single file may be split into two or more files and the like without departing from the scope of the present inventive concept.

As further illustrated in FIG. 3, the application programs 354 may an interactive audio interface 351, a secure file transfer tool 352, a secure electronic interface 353 and an external database 357 in accordance with some embodiments of the inventive concept. While the present inventive concept is illustrated, for example, with reference to the interactive audio interface 351, the secure file transfer tool 352, the secure electronic interface 353 and the external database 357 being application programs in FIG. 3, as will be appreciated by those of skill in the art, other configurations may also be utilized while still benefiting from the teachings of the present inventive concept. For example the interactive audio interface 351, the secure file transfer tool 352, the secure electronic interface 353 and the external database 357 may also be incorporated into the operating system 352 or other such logical division of the data processing system 200. Thus, the present inventive concept should not be construed as limited to the configuration of FIG. 3, but is intended to encompass any configuration capable of carrying out the operations described herein.

Furthermore, while the interactive audio interface 351, the secure file transfer tool 352, the secure electronic interface 353 and the external database 357 are illustrated in a single data processing system, as will be appreciated by those of skill in the art, such functionality may be distributed across one or more data processing systems. Thus, the present inventive concept should not be construed as limited to the configuration illustrated in FIGS. 2 and 3, but may be provided by other arrangements and/or divisions of function between data processing systems.

Referring now to FIGS. 2 and 3, as discussed above, embodiments of the present inventive concept provide systems for recording electronic data records. The system includes an interactive audio interface 351 configured to receive a real time voice command 364, parse the real time voice command for keywords and values 366 and trigger the values to be stored. In some embodiments, the interactive audio interface 351 can be an Amazon Echo, a Google Home or Apple HomePod. The user, typically a clinician, speaks a particular voice command, for example, "Echo Tell Margaret chart" (discussed further below) and this triggers the interactive audio interface to parse the command for keywords (chart) and locate the values associated therewith. For example, if the keywords were " . . . chart blood pressure," the associated value may be 120/80. These values 366 are then triggered to be stored in a database 357 along with a time stamp 361. The external database 357 is configured to store the values 366 parsed from the real time voice command 364 and associate a time stamp 361 with the stored values 366. In some embodiments, a look up table may be used to locate a physical location associated with the values 366 being stored. As used herein, physical location may refer to a room number, a bed number or any other identifier that can be used to associate the audio interface with the patient. The look up table uses a location of the interactive audio interface 351 to determine the physical location associated with the values 366. This physical location may be stored in the database 354 with the timestamp 361 and values 366. In some embodiments, this database 354 may be encrypted. In some embodiments, the identification of the interactive audio interface 351 in the look up table may be a hash of the actual identifier for the device, for example, a 128 bit hash of the identifier for the device. It will be understood that in some embodiments the physical location or room/bed number associated with the interactive audio device 351 may not be determined until the values and timestamp are communicated to the secure datacenter associated with the organization.

The values 366, timestamp 361 and option location are transferred to the secure datacenter using the secure file transfer tool 352. The secure datacenter could be, for example, a hospital network. Once the values, timestamp and optional location are securely transferred, they are stored in the appropriate patient/data records in electronic records module, for example, electronic medical records. In some embodiments, once the values are stored in the appropriate records, these values are verified by a clinician before making these values a permanent part of the record.

In some embodiments, a secure electronic interface 353 is provided in the secure datacenter. The electronic interface 353 is configured to receive the transferred stored values and time stamp from the secure file transfer tool. The physical location associated with the stored values and the time stamp may be determined at this point if it has not be previously determined.

Although embodiments of the present inventive concept are directed to using the interactive audio interface 351 to verbally enter data into data records. However, it will understood, that interactive audio interface 351 may also be used to provide patient satisfaction applications and/or information.

Figure 4:
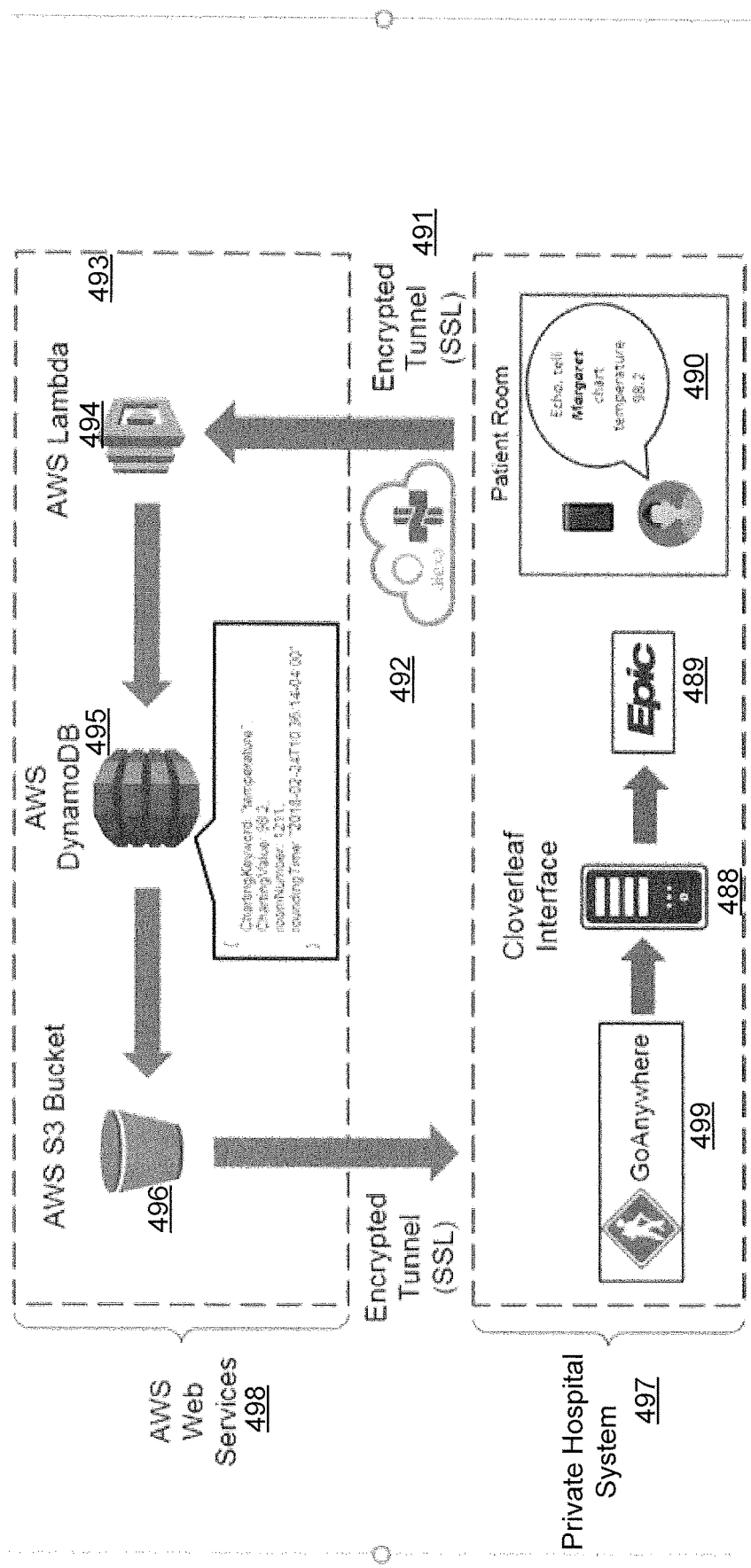
FIG. 4 is a block diagram of a detailed system in accordance with embodiments of the present inventive concept utilizing an Amazon Echo in a clinical environment.

Referring now to FIG. 4, a specific example of entering patient data into an EMR using the Amazon Echo will be discussed. Thus, in this example, the interactive audio interface 105 (smart speaker/virtual assistant) will be called "Echo"). The process begins at block 490 when the clinician speaks the command "Echo tell Margaret . . . "—fill in the patient data the clinician wants to be stored in the patient record. It will be understood that the process of capturing and storing discrete data elements (patient data) into the EMR (160—FIG. 1) begins with building custom Echo skills that are activated with a key word and phrase. The natural language processing (VUI 130—FIG. 1) built into the Echo device translates the human utterance (voice) into a command recognized by a software program designed to parse the data elements from the human utterance. In this particular example, the commands are:

Echo Tell Margaret chart 3P's

Echo Tell Margaret chart Pain 5

Echo Tell Margaret chart POSS 2 (Pasero Opioid-induced sedation scale)

Echo Tell Margaret chart vitals blood pressure 120 over 80

Echo Tell Margaret chart vitals temperature <decimal value> e.g. "98.6"

Echo Tell Margaret chart vitals pulse (integer value) e.g. "72"

Echo Tell Margaret chart urinary output <integer value in ml> e.g. "100 ml"

Echo Tell Margaret chart meals <"breakfast", "lunch", "dinner", "snack">, numerical percentage <0-100%> e.g. "meals breakfast 75%"

Echo Tell Margaret chart activity <"resting", "Turned", "Stand at bedside", "Stand and pivot", "Ambulate in hall", "Ambulate in hallway"<integer value> feet > e.g. Ambulate in hallway 15 feet Thus, in this example, the keyword "Margaret" was assigned to uniquely identify this particular program for other Echo commands. The words contained in the command that follow "Margaret" are the keywords and values specific to the parameter that a clinician is entering into the patient record to be stored in the EMR. The Echo converts the natural language to text, and the program parses the text for keywords and values; keywords are associated with a value for example "chart pulse" with a value of "70".

As further illustrated, the information retrieved using the series of keywords and values recognized by the Echo is communicated over an encrypted tunnel (Secure Sockets Layer (SSL) tunnel) 491 through the cloud 492. The information orally provided by the clinician to the Echo and recognized by the Echo is stored (as values) in a database with a corresponding timestamp to document when the event occurred. In this example, DynamoDB 495, an AWS cloud based database system was used to store the values and the timestamps. Before the data is stored in the DynamoDB database system 495, the values are processed by a custom software algorithm (AWB Lambda 494). This software processes the data and provides the processed data to the database, in this case DynamoDB 495. As illustrated in FIG.

4, once the data is stored in the database 495, the data has been matched with the room number associated with the data and, therefore, associated with the patient. In other words, the keyword, values and timestamp are entered into the database 495 along with an identifier which associated the entry to the Echo device that recorded the command. In this embodiments, a "room lookup" was performed matching the ID of the echo that recorded the command with the room number where the Echo was physically installed. As illustrated, this room number is also stored in the DynamoDB record associated with the command. In some embodiments, for even greater security and anonymity, the association with the room number may be performed later in the process after the data has been transferred into the Hospitals internal systems 497. In some embodiments, the identification of the Echo in the look up table may be a hash of the actual identifier for the Echo, for example, a 128 bit hash of the identifier for the device.

It will be understood that embodiments of the present inventive concept do not use the patient's name, medical record or any other identifying information is not used or recorded when the data is transmitted to or stored in the cloud. The association of the clinical data to the actual patient is performed later in the process within the hospitals EMR and interface systems 497 as will be discussed below.

Once the patient/clinical data is stored in the cloud and ready to be imported into the EMR, the DynamoDB entry is transferred into an AWS S3 bucket 496. S3 is a cloud based storage system hosted by Amazon. In the example embodiments, the data was transferred into the AWS S3 bucket 496 because the hospital uses a secure file transfer system called "GoAnywhere" 499 which has a built-in secure S3 transfer tool making it very easy to periodically (for example every minute) request and download files from S3 into GoAnywhere 499. It will be understood that this implementation is provided as a real world example only and that embodiments of the present inventive concept are not limited thereby. Other file transfer devices/applications may be used without departing from the scope of the present inventive concept.

Referring again to FIG. 4, GoAnywhere 499 is a service running on a server within the hospital datacenter. Once the file containing the clinical/patient data is within the hospital datacenter 497, a room lookup is performed. In these embodiments, a Cloverleaf interface engine 488 is used to grab the file from GoAnywhere 499, parse the keywords and convert them into an "HL7" format that can be recognized the hospital's EMR. It will be understood that, as discussed above, instead of matching the room number with the data in the DynamoBD as discussed above, the file lookup method using the table lookup that associates the hashed ID of the Echo that recorded the command to a patient room number may be performed at this point in some embodiments. In these alternative embodiments, the lookup will be performed behind the hospital's firewall and, therefore, may be more secure.

The clinical data and room number are sent via "HL7" interface to the EMR 489 (Epic). The EMR then inserts the values into the relevant part of the flowsheet for viewing. Because no authentication was performed when the command was entered in the Echo, the data is entered as non-verified data. The clinician then views the flowsheet after it is completed and validates the data entry.

It will be understood that the process discussed with respect to FIG. 4 is provided as a real world example only and, therefore, embodiments of the present inventive concept are not limited thereto. For example, in some embodiments, fast healthcare interoperability resource (FHIR) interface or application programming interface (API) may be use to securely transfer data to the EMR without departing from the scope of the present inventive concept.

Some embodiments of the present inventive concept may support authentication methods such as voice recognition, one time passwords, integration with nurse tracking system, and the like to ensure that clinical data was entered by an authorized caregiver.

Figure 5:
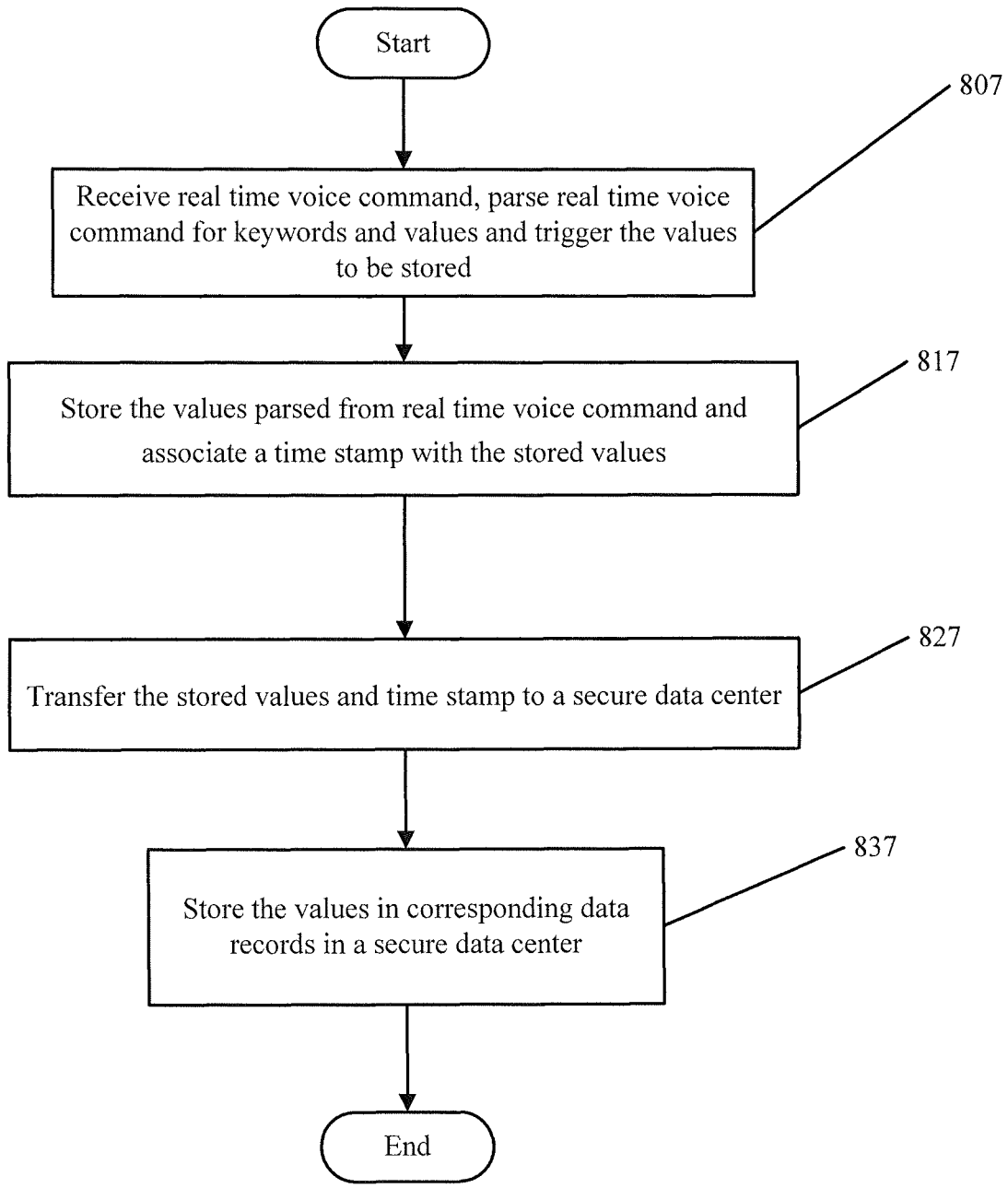
FIG. 5 is a flowchart illustrating methods in accordance with various embodiments of the present inventive concept.

Operations in accordance with various embodiments of the inventive concept will now be discussed with respect to the flowchart of FIG. 5. Operations for hands free recording of electronic data records using an interactive audio interface begin at block 807 by receiving a real time voice command, parsing the real time voice command for keywords and values and triggering the values to be stored. As discussed above, the interactive audio interface could be one of many of these types of interfaces without departing from the present inventive concept. The values parsed from the real time voice command are stored and a time stamp is associated with the stored values (block 817). The stored values and time stamp are transferred to a secure datacenter (block 827). For example, the secure datacenter may be a datacenter associated with a hospital. The values are stored in corresponding data records in the secure datacenter (block 837).

As discussed above, at some point in the process, the values are associated with a physical location (room/bed number) of the interactive audio interface such that the values can be stored in the proper data or patient record. The determination of the physical location of the interactive audio interface may be done at various point in the process without departing from the scope of the present inventive concept.

It is very important that the values stored are accurate and are stored in the proper record. Thus, once the values are stored in the EMR, these values are verified by a clinician before the values are made permanent.

As further discussed above, beyond receiving voice commands associated with electronic data records, the interactive audio interface discussed herein is configured to receive requests for patient satisfaction applications and/or information as discussed above. Thus, the presence of the interactive audio interface in accordance with embodiments discussed herein not only increases efficiency of clinicians, but may also provide a more satisfactory experience for the patients.

Example embodiments are described above with reference to block diagrams and/or flowchart illustrations of methods, devices, systems and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, example embodiments may be implemented in hardware and/or in software (including firmware, resident software, micro-code, etc.). Furthermore, example embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of example embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a field programmable gate array (FPGA), or a programmed digital signal processor, a programmed logic controller (PLC), or microcontroller.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

In the drawings and specification, there have been disclosed example embodiments of the inventive concept. Although specific terms are employed, they are used in a generic and descriptive sense only and not for purposes of limitation, the scope of the inventive concept being defined by the following claims.

That which is claimed:

1. A system for recording electronic data records, the system comprising:
    an interactive audio interface configured to receive a real time voice command, parse the real time voice command for keywords and values and trigger the values to be stored in a cloud-based database system without patient-identifying information, wherein the real time voice commands are associated with a time stamp;
    a secure file transfer tool configured to transfer the stored values and time stamp from the cloud-based database system to a secure datacenter;
    an electronic interface in the secure datacenter, wherein the electronic interface is configured to receive the transferred stored values and time stamp from the secure file transfer tool and to associate a physical location with the transferred stored values and the time stamp, wherein the physical location comprises an identifier that associates the interactive audio interface with a patient-identifiable data record; and
    an electronic records module in the secure datacenter configured to store the transferred stored values in corresponding patient-identifiable data records.

2. The system of claim 1, wherein the physical location is one of a room number, bed number and any identifier of physical location associated with the interactive audio interface and wherein the physical location is located by matching an identifier associated with the interactive audio interface to the physical location in a look up table.

3. The system of claim 1, wherein the transferred stored values in the electronic records module are verified before becoming a permanent part of the patient-identifiable data record.

4. The system of claim 1, wherein the electronic records module comprises an electronic medical records data module and wherein the corresponding patient-identifiable data records are patient data records.

5. The system of claim 1, wherein the interactive audio interface is further configured to receive a request for patient satisfaction applications and/or information and provide the requested patient satisfaction applications and/or information.

6. The system of claim 1, wherein the interactive audio interface is configured to select medically relevant data elements from a conversation or dictation for documentation in the stored values.

7. The system of claim 1, wherein the association of the physical location with the transferred stored values and the time stamp is performed after the stored values are transferred into the secure datacenter.

8. A method for hands free recording of electronic data records using an interactive audio interface, the method comprising:
    receiving a real time voice command, parsing the real time voice command for keywords and values and triggering the values to be stored;

storing the values parsed from the real time voice command and associating a time stamp with the stored values, wherein the stored values are stored in a cloud-based database system without patient identifying information;

transferring the stored values and time stamp to a secure datacenter;

receiving the transferred stored values and time stamp by an electronic interface in the secure datacenter from a secure file transfer tool and associating the transferred stored values with a physical location after transferring the stored values and time stamp from the cloud-based database system to the secure datacenter, wherein the physical location comprises an identifier that associates the interactive audio interface with the patient-identifiable data record; and storing the transferred stored values in corresponding patient-identifiable data records in the secure datacenter.

9. The method of claim 8, wherein the physical location is one of a room number, bed number and any identifier of physical location associated with the interactive audio interface, the method further comprising locating the physical location by matching an identifier associated with the interactive audio interface to the physical location in a look up table.

10. The method of claim 8, further comprising verifying the transferred stored values before becoming a permanent part of the data record.

11. The method of claim 8, wherein the corresponding patient-identifiable data records are patient data records.

12. The method of claim 8, further comprising: receiving a request for patient satisfaction applications and/or information; and providing the requested patient satisfaction applications and/or information.

13. A computer program product for hands free recording of electronic data records, the computer program product comprising:

a non-transitory computer readable storage medium having computer readable program code embodied in the non-transitory computer readable storage medium and a processor for executing the computer readable program code in the non-transitory computer readable storage medium, the computer readable program code comprising:

computer readable program code to receive a real time voice command, parse the real time voice command for keywords and values and trigger the values to be stored;

computer readable program code to store the values parsed from the real time voice command and associate a time stamp with the stored values, wherein the stored values are stored in a cloud-based database system without patient-identifying information;

computer readable program code to transfer the stored values and time stamp to a secure datacenter with a secure file transfer tool;

computer readable program code to receive the transferred stored values and time stamp from the secure file transfer tool; and computer readable program code to associate a physical location with the transferred stored values and the time stamp, wherein the physical location comprises an identifier that associates the interactive audio interface with the patient-identifiable data record; and computer readable program code to store the transferred stored values in corresponding patient-identifiable data records in the secure datacenter.

14. The computer program product of claim 13, wherein the physical location is one of a room number, bed number and any identifier of physical location associated with an interactive audio interface, the computer program product further comprising computer readable program code to locate the physical location by matching an identifier associated with the interactive audio interface to the physical location in a look up table.

15. The computer program product of claim 13, further comprising computer readable program code to verify the stored values before becoming a permanent part of the patient-identifiable data record.

* * * * *